United States Patent
Galyuk

(10) Patent No.: US 10,814,248 B2
(45) Date of Patent: *Oct. 27, 2020

(54) METHODS TO REDUCE CHLOROPHYLL CO-EXTRACTION THROUGH EXTRACTION OF SELECT MOIETIES ESSENTIAL OILS AND AROMATIC ISOLATES

(71) Applicant: Yevgeniy Galyuk, Sherman Oaks, CA (US)

(72) Inventor: Yevgeniy Galyuk, Sherman Oaks, CA (US)

(73) Assignee: Capna IP Capital, LLC, Studio City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/681,765

(22) Filed: Nov. 12, 2019

(65) Prior Publication Data

US 2020/0094163 A1 Mar. 26, 2020

Related U.S. Application Data

(60) Continuation-in-part of application No. 16/023,531, filed on Jun. 29, 2018, now Pat. No. 10,507,407, (Continued)

(51) Int. Cl.
*B01D 11/02* (2006.01)
*C11B 9/02* (2006.01)
(Continued)

(52) U.S. Cl.
CPC .......... *B01D 11/0219* (2013.01); *B01D 11/02* (2013.01); *B01D 11/028* (2013.01);
(Continued)

(58) Field of Classification Search
CPC ... B01D 11/02; B01D 11/0219; B01D 11/028; B01D 11/0288; B01D 11/0292; B01D 11/0296; C11B 9/025; C07D 311/78
See application file for complete search history.

(56) References Cited

U.S. PATENT DOCUMENTS

| | | | |
|---|---|---|---|
| 2004/0110828 A1* | 6/2004 | Chowdhury | A61K 31/353 514/454 |
| 2013/0079531 A1* | 3/2013 | Barringer | C07D 311/78 549/390 |

(Continued)

OTHER PUBLICATIONS

Ali, A., et al., The safety and efficiency of 3% cannabis seeds extract cream for reducttion of human cheek skin sebum and erythema content, Pak. J. Pharm. Sci., vol. 28, No. 4, pp. 1389-1395 (Year: 2015).*

(Continued)

*Primary Examiner* — Yate' K Cutliff
(74) *Attorney, Agent, or Firm* — Patnstr®, APC; Tom Brody; Peter Jon Gluck, Esq.

(57) ABSTRACT

A system, machines and methods for extracting select moieties, flavonoids, and essential oils from plant material without co-extracting chlorophyll, lipids and other undesirable constituents from plants. Super-cooled extraction techniques are taught. Likewise, according to embodiments methods provides 100% grain ethyl alcohol extract with a concentration of chlorophyll that is below 1%.

7 Claims, 3 Drawing Sheets

Related U.S. Application Data which is a division of application No. 15/488,341, filed on Apr. 14, 2017, now Pat. No. 10,035,081.

(60) Provisional application No. 62/322,751, filed on Apr. 14, 2016.

(51) Int. Cl.
*F25B 7/00* (2006.01)
*C07D 311/78* (2006.01)

(52) U.S. Cl.
CPC ...... *B01D 11/0288* (2013.01); *B01D 11/0292* (2013.01); *B01D 11/0296* (2013.01); *C11B 9/025* (2013.01); *F25B 7/00* (2013.01); *C07D 311/78* (2013.01)

(56) References Cited

U.S. PATENT DOCUMENTS

2016/0228787 A1* 8/2016 Payack ............... B01D 3/343
2017/0333503 A1* 11/2017 Ayres ............... A61K 36/185
2018/0271827 A1* 9/2018 Heimark ........... B01D 11/0288

OTHER PUBLICATIONS

Wikipedia, List of boiling and freezing information of solvents, 3 pages (Year: 2020).*

Burdick & Jackson, Honeywell sub., Freezing point, Macro, 1us edu., 2 pages (Year: 2020).*

The Engineering Tool Box, Ethanol Freeze Protected Water Solutions, 1 page (Year: 2020).*

Emre, Aktay, Polat, and Vardt, (2007) Effects of benzo(a)pyrene and ethanol on oxidative stress of brain, lung tissues and lung morphology in rats. Chinese Journal of Physiology. 50(3):143-148. Wolters Kluwer, South Holland, Netherlands.

Regert, Alexandre, Thomas, and Lattuati-Derieux. (2006) Molecular characterisation of birch bark tar by headspace solid-phase microextraction gas chromatography-mass spectroscopy, J. Chromatography A. 1101:245-253. Elsevier, New York. NY.

Fraudette, (2016) No. 9. Vacuum Furnace Reference Series, Understanding vacuum and vacuum measurement. Solar Manufacturing. Souderton, PA. 9 pages.

Norgaard, Hansen, Sorli et al. (2013) Pulmonary toxicity of perfluorinated silane-based nanofilm spray products: solvent dependency. Toxicological Sciences. 137(1):179-188. Oxford Univ. Press, Oxford, UK.

Ponomarenko, Yang, Mohiuddin, et al. (2009) Effect of high-K environment on charge carrier mobility in graphene. Phys. Rev. Lett. 102:206603. American Physical Society, College Park, MD.

Johnson (2004) Safety assessment of MIBK (methyl isoburyl ketone). International J. Toxicology. 23 (Suppl. 1) 29-57. Published by SAGE Publishing, Thousand Oaks. CA.

* cited by examiner

METHODS TO REDUCE CHLOROPHYLL CO-EXTRACTION THROUGH EXTRACTION OF SELECT MOIETIES ESSENTIAL OILS AND AROMATIC ISOLATES

CROSS REFERENCE TO RELATED APPLICATIONS

This application claims priority benefit of U.S. Provisional Ser. No. 62/322,751 filed Apr. 14, 2016, and of U.S. Ser. No. 15/488,341 filed Apr. 14, 2017, now U.S. Pat. No. 10,035,081, issued Jul. 31, 2018, each of which is incorporated by reference herein in its entirety. This application also claims priority benefit from U.S. Ser. No. 16/023,531, which is incorporated by reference in its entirety.

FIELD OF THE DISCLOSURE

The present disclosure relates to systems and methods for solvent-free processing of plant materials. The system and methods may use other materials, in place of a solvent, such as oil or an ionic liquid, for extracting plant material or for further extraction of a plant extract, followed by purification by distillation, optionally with heat-induced chemical transformation of natural products in the plant material.

BACKGROUND OF THE DISCLOSURE

This disclosure relates to ways of extracting and concentrating cannabinoids and terpenes from plant substrates including hemp, and particularly modifying the characteristics of the solvent to by-pass undesired constituents of plants throughout the extraction process.

Extraction of industrial hemp and cannabis can be done via many methods, using a wide array of FDA approved food grade solvents. The most commonly used solvents are hydrocarbons such as hexane, pentane, butane or propane. Lipid based solvents such as canola oil, soybean oil, olive oil, flax seed oil, hemp oil are also commonly used in hemp and cannabis extraction methods. Super critical $CO_2$ is also commonly used in cannabis extraction, but the expensive machinery and the post extraction steps required to purify an SFE extract (supercritical fluid extraction) of undesired plant lipids, makes SFE the least desirable method for any commercial processor.

Several drawbacks of hydrocarbon extraction methods have been recognized. The most prominent of these drawbacks is the volatility of hydrocarbon solvents. The cost associated with retrofitting a laboratory with explosion proof electronics, ventilation fans etc. create enormous start-up costs. Second, pure hydrocarbon solvents such as N-butane or N-hexane are extremely difficult to obtain and therefore are hardly ever used for cannabis extract production. The majority of extracts are created with inferior, low quality butane that contains additives and impurities.

Lipid based extractions are much safer and healthier than hydrocarbons, but separating the cannabinoids or flavonoids from a lipid emulsion requires a thorough understanding of chemistry, as well as expensive distillation devices.

Various states and local governments are now legalizing cannabis for medical and recreational use. This creates an entire market of DIY extractions which are obtained through low quality, impure, hydrocarbons such as butane and propane. These extractions not only pose a threat to the consumer, but to the manufacturers as well. Numerous instances have been recorded where home made laboratories have exploded or caught fire because of the unsafe practices of DIY manufacturers.

SUMMARY OF THE DISCLOSURE

The present invention includes a novel extraction process that yields a clean cannabinoid/terpene extract devoid of plant lipids and chlorophyll. Various methods of the present invention are designed to be performed in a food grade manufacturing environment but can also be achieved by a novice manufacturer with minimal investment.

The term extract as used herein should be broadly understood to include both cannabinoid and terpene concentrates and extracts of plant substrate. The terms cannabinoids and terpenes should be construed broadly to include their various isomers.

In a preferred, non-limiting embodiment, the term solvent as used herein should be understood to describe 100% grain ethanol.

The method of the present disclosure includes lowering the temperature of the solvent below −1 C. Preferably to a range of −30 C to −50 C.

The method of the present invention requires the solvent to contact the plant substrate for a period of time between 1 minute and 40 minutes.

The method of the present invention includes a filtration step carried out at a temperature between −1 C and −50 C.

The method of the present invention includes a reduction step which can be accomplished via atmospheric evaporation of the solvent.

The method of the present invention includes a solvent recovery step which can be accomplished via simple distillation or rotary evaporator apparatus.

The method of the present invention includes a purging step under vacuum to remove remaining solvent from the extract.

The present disclosure provide a safer and more reliable extraction process for extracting a plant substrate comprising, in combination, (i) pre-processing comprising lowering the temperature of a solvent to a range of −30 degrees C. to −50 degrees C., (ii) contacting at −30 degrees C. to −50 degrees C., wherein there is a contacting time between the plant substrate and the solvent to create an emulsion, (iii) evaporating for reduction of the emulsion by means of atmospheric evaporation of the solvent, (iv) recovering for recovery of the solvent from the emulsion, (v) purging whereby a resultory extract is substantially free of any lipids and chlorophyll, wherein optionally, (a) the solvent is not 100% grain alcohol, or (b) wherein the solvent is 95% ethanol and 5% of a solvent that is another solvent that does not comprise ethanol, or (c) the solvent is at least one solvent-like material selected from the group consisting essentially of heptane, hexane, isopropyl alcohol, or methanol, or (d) wherein the solvent is not 100% ethanol.

Moreover, the present disclosure provides the above extraction process, wherein the solvent is not 100% grain alcohol; or wherein the solvent is 95% ethanol and 5% of a solvent that is another solvent that does not comprise ethanol; or wherein the solvent is at least one solvent-like material selected from the group consisting essentially of heptane, hexane, isopropyl alcohol, or methanol.

In composition of matter embodiments, the present disclosure provides a plant substrate extract produced by the above-disclosed extraction process. In similar composition of matter embodiments, the present disclosure provides a composition that comprises a plant substrate extract produced by the above-disclosed extraction process. In additional composition of matter embodiments, the disclosure provides any of the above-disclosed compositions, wherein the composition is one of: (i) a liquid at room temperature (23 degrees C.), (ii) a composition that comprises an oil, and wherein the oil is optionally an essential oil, a vegetable oil, or a mineral oil, (iii) a composition that contains less than 5% by weight an oil, or that contains less than 5% by volume an oil, as determinable at room temperature.

In another process embodiments, the present disclosure any one of the above processes, wherein the wherein the contacting at –30 degrees C. to –50 degrees C., is at least 5 minutes in the range of: (i) –30 degrees C. to –35 degrees C., (ii) –35 degrees C. to –40 degrees C., (iii) –40 degrees C. to –45 degrees C., or (iv) –45 degrees C. to –50 degrees C. In further process embodiments, the present disclosure any one of the above processes, wherein the contacting time that is at least 5 minutes in the indicated temperature range is for a period of time in the indicated temperature range that has a continuous and uninterrupted duration within that temperature range of: (i) 5 minutes to 10 minutes, or (ii) 10 minutes to 15 minutes, or (iii) 15 minutes to 20 minutes, or (iv) 20 minutes to 25 minutes, or (v) 5 minutes to 15 minutes, or (vi) 5 minutes to 20 minutes.

In yet another process embodiment, the present disclosure provides any one of the above processes, wherein the solvent consists of a mixture of ethanol and a non-ethanol solvent, and wherein this mixture is at one of the following ratios, wherein the percentage value is by volume of the ethanol and of the non-ethanol solvent, wherein the volume of the ethanol and the volume of the non-ethanol solvent are each measured prior to mixing the ethanol with the non-ethanol solvent, wherein the ratio is one of: (i) 95% ethanol plus 5% non-ethanol solvent, (ii) 90% ethanol plus 10% non-ethanol solvent, (iii) 85% ethanol plus 15% non-ethanol solvent, (iv) 80% ethanol plus 20% non-ethanol solvent, (v) 75% ethanol plus 25% non-ethanol solvent, (vi) 70% ethanol plus 30% non-ethanol solvent, (vii) 65% ethanol plus 35% non-ethanol solvent, (viii) 60% ethanol plus 40% non-ethanol solvent, (ix) 55% ethanol plus 45% non-ethanol solvent, (x) 50% ethanol plus 50% non-ethanol solvent.

In embodiments relating to alternative solvents, or relating to additional types of solvents, the present disclosure provides any of the above-disclosed processes, wherein the solvent consists of (or comprises) methanol, isopropyl alcohol, or acetonitrile, or mixtures thereof. Also, in embodiments relating to alternative solvents, or relating to additional types of solvents, the present disclosure provides any of the above-disclosed processes, wherein the solvent comprises about 2%, or about 4%, or about 8%, or about 10%, or about 12%, or about 14% or about 16%, or about 18%, or about 20%, or about 25%, or about 30%, or about 35%, or about 40%, or about 45%, or about 50%, or about 55%, or about 60%, or about 65%, or about 70%, or about 75%, or about 80%, methanol, or isopropyl alcohol, or acetonitrile. In exclusionary embodiments, the system, devices, structures, reagents, fluids, solutions, emulsions, extracts, and methods can exclude any system, fluid, solution, extract, or emulsion, that consists (or that comprises) methanol, isopropyl alcohol, or acetonitrile, or mixtures thereof, that occur at one of the above-disclosed concentrations.

BRIEF DESCRIPTIONS OF THE DRAWINGS

DETAILED DESCRIPTION

The present inventor has evolved systems for extraction using traditional techniques along with super-cooling and achieved unexpected results.

Figure 1:
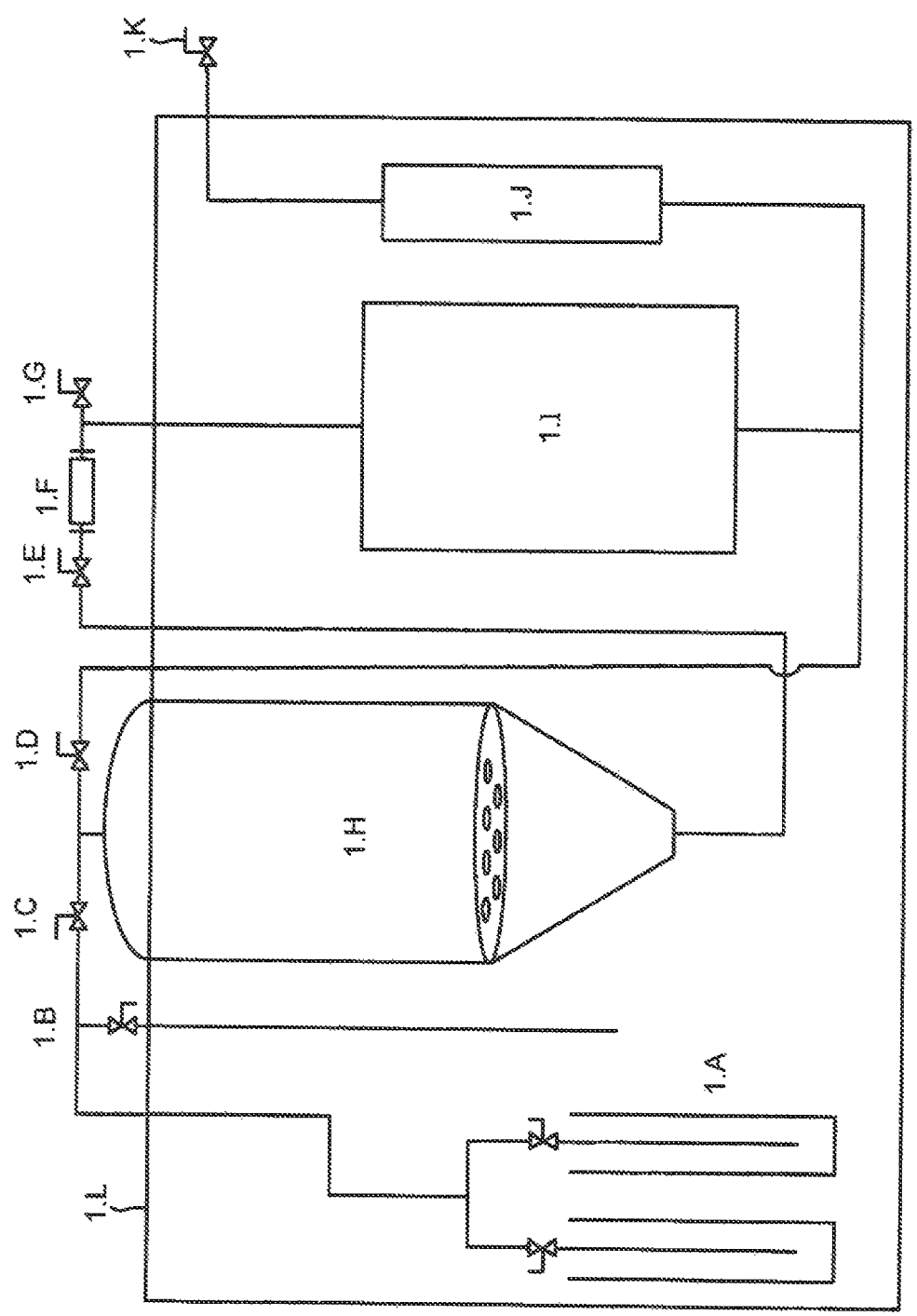
FIG. 1 is a schematic of a system which performs claimed steps in accordance with the present invention.

FIG. 1 illustrates is an inventive vessel—wet plumbing and freezer compartment assembly which has produced unexpectedly better results than predicted. Without limiting the technical description to a single mechanism, it is known that super-cooling processes have driven these unexpected results with this system. Solvent storage 1.A is operatively and communicatively linked to cold air intake valve 1B via known lines to those skilled in the art as shown. Solvent flooding valve 1.C then runs via lines to the emulsion return valve 1.D as shown above extraction tank 1.H. Emulsion collection valve 1.E is then ported through sight glass 1.F and down to Extraction tank 1.H and is connected to inline filter housing 1.J along to evacuation valve 1.K. The improvement of enclosure within 1.L the ultra-low freezer compartment has resulted in unexpectedly better results.

Figure 2:
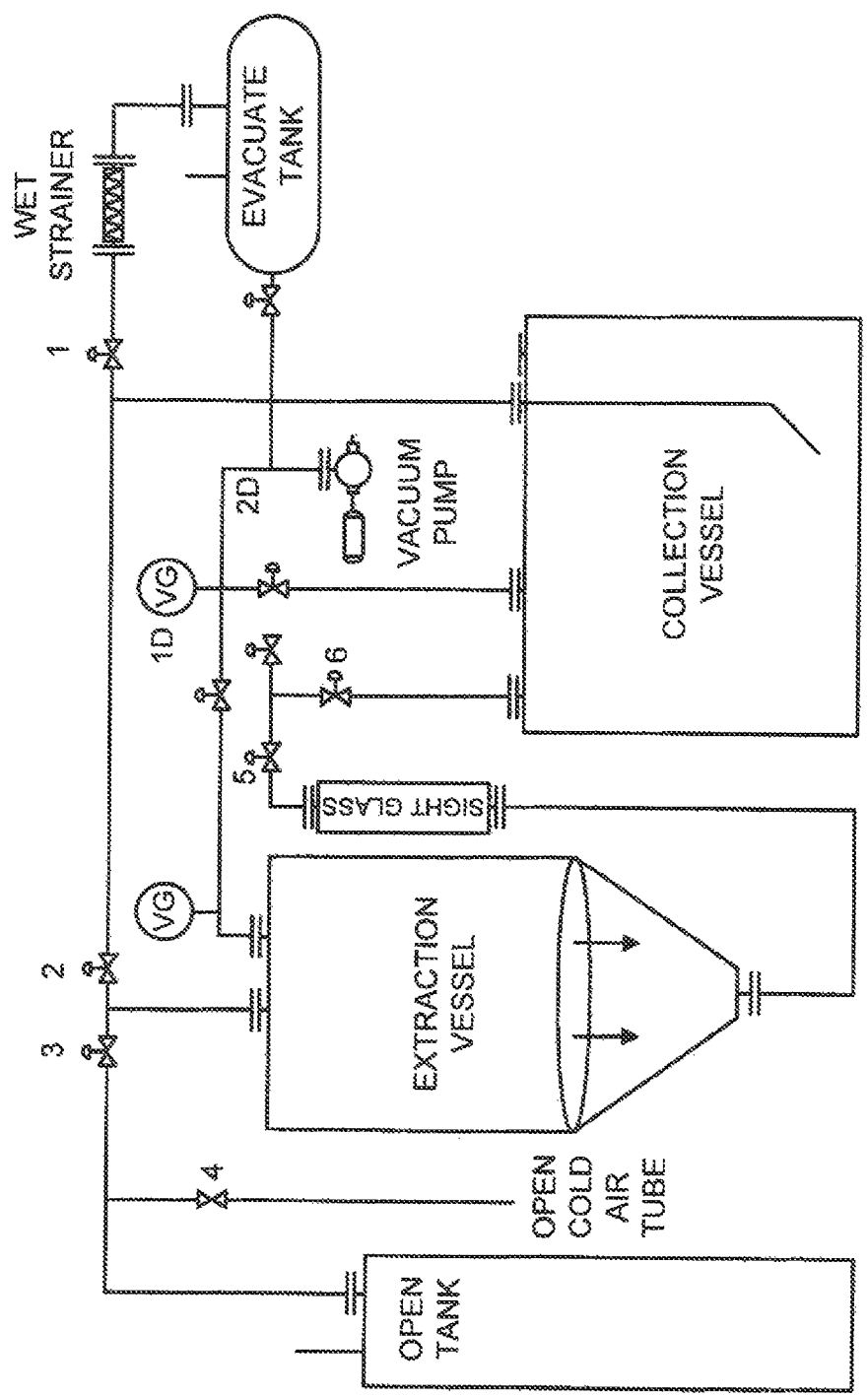
FIG. 2 is a is a schematic of a system which performs claimed steps in accordance with the present invention, showing how the same is improved over prior art technology.
Figure 3:
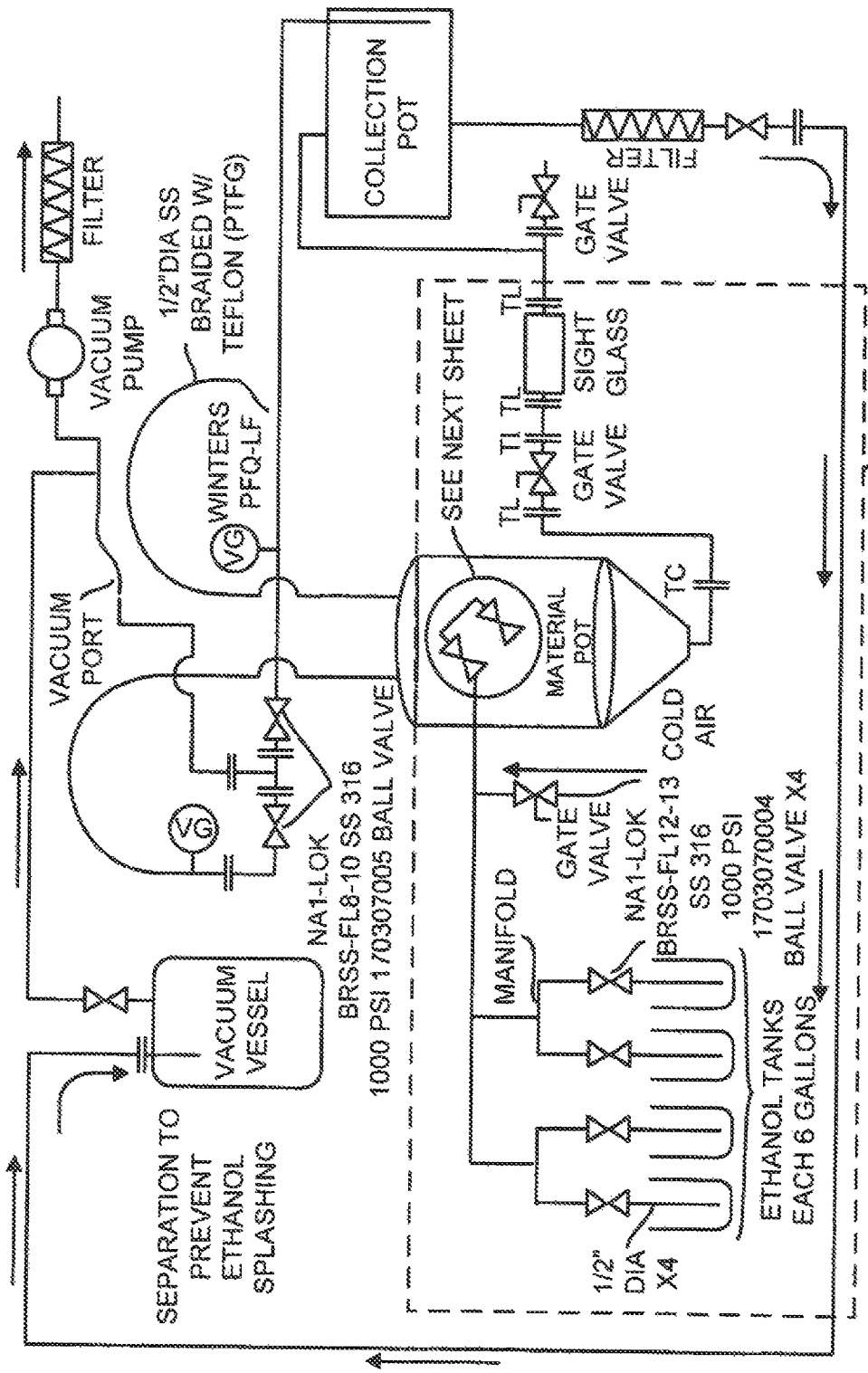
FIG. 3 is a schematic of a system which performs claimed steps in accordance with the present invention, for select moieties and essential oils.

FIG. 2 also shows the plumbing and how the prior arts systems were improved, while FIG. 3 shows optimized systems for select moieties, as discussed above and claimed below. Regarding both FIGS. 2 and 3, FIG. 2 shows control valves 1, 2, 3, 4 and 6 with gate valve 4, vacuum gauge 1D.

As discussed in Ser. No. 62/322,751, Step 3 of the present invention includes for the necessary amount of contact time between plant substrate and solvent to create a heavy yielding extract emulsion. Contact time should be carried out at a temperature range of –30 C to –50 C.

Step 4 of the present invention includes a filtration step to remove all plant material from the solvent. This step is carried out at a temperature range of –30 C to –50 C.

Step 5a of the present invention includes a process for reduction of the concentrate emulsion by means of atmospheric evaporation of the solvent.

Step 5b of the present invention includes a process for recovery of the solvent from the concentrate emulsion.

Step 6a and 6b of the present invention include a process by which a concentrate can be purged of solvent to produce a nutraceutical in accordance with the present invention.

FIG. 2 is a flow chart of the method which includes the use of an extraction apparatus in accordance with the present invention.

Steps 1 and 2 include the pre-processing step of freezing the solvent and plant substrate to desired temperature between –30 C and –50 C.

Step 3 of the present invention includes the pre-processing step of chilling the extraction apparatus to a temperature between –30 C and –50 C via cryo chiller.

Step 4 of the present invention requires the chilled solvent to be added to pre-chilled extraction vessel.

Step 5 of the present invention requires the chilled plant substrate to be added to extraction vessel.

Step 6 of the present invention includes allowing the solvent to contact the plant substrate for a desired time between 1 minute and 60 minutes.

Step 7a of the present invention includes a solvent evacuation step via positive pressure.

Step 7b of the present invention includes a solvent evacuation step via negative pressure.

Step 8 of the present invention includes a process in which the solvent and plant substrate are separated via inline filtration.

Steps 1 and 2 of the flow chart represent a pre-processing step which includes a method of chilling the solvent and plant substrate to a desired temperature between −1 C and −50 C, preferably in a range between −30 C and −50 C, ideally in a range between −40 C and −45 C. In one embodiment of the present invention, step 1 can be carried out via ultra low freezer set to preferred temperature. In another embodiment of the present invention, step 1 can be carried out via re-circulating cryo chiller connected to a holding vessel filled with solvent.

Step 2 of a process of the present invention can be carried out via ultra low freezer wherein the plant substrate is stored in the ultra low freezer to achieve the desired temperature between −40 C and −45 C. Step 2 of FIG. 1 in the present invention includes, the plant substrate is placed inside of a micro mesh bag and inserted into the extraction vessel of prior to step 3 of FIG. 1 of the provided method.

Step 3 of a process includes that the extraction vessel is stainless steel, aluminum, borosilicate, or polytetrafluoroethylene (PTFE). Step 3 of FIG. 1 includes that the extraction vessel is set inside of a freezer able to maintain the desired temperate of −50 C. Step 3 of FIG. 1 includes the addition of chilled solvent to extraction vessel. Step 3 of FIG. 1 includes a contact time between solvent and plant substrate to allow desired solubles to enter the solvent and create an emulsion rich in essential oils, cannabinoids and terpenes. Step third includes that the desired contact time is between 1 minute and 60 minutes, preferably between 3 and 10 minutes, ideally between 2 and 5 minutes. Step 4 includes a method for separating the cannabinoid rich emulsion from plant substrate.

Step 4, includes a collection vessel is placed into the freezer in which Step 3 of was carried out. Step 4 of includes that a strainer is placed onto the collection vessel and the plant substrate is placed into the strainer to allow for a gravity assisted drain. The draining process must be carried out in the preferred temperature range of −40 C and −45 C to exclude the co-extraction of lipids and chlorophyll during the Step of described. In another embodiment of Step 4, the plant substrate held in a micron bag through Step 3. In this embodiment the plant material is removed with the micron bag. In another embodiment of Step 4 the micron bag filled with the plant substrate is placed inside the strainer to allow the residual solvent to drain into the collection vessel through gravity assist. In another embodiment of Step 4, the collected cannabinoid rich emulsion is then further filtered to remove small particles via Buchner funnel and Erlenmeyer flask with vacuum assist. In this embodiment of the filtration Step 4 ambient room temperature is acceptable as the bulk of plant substrate has been removed via strainer and micron bag.

Emulsions.

Guidance for characterizing and identifying emulsions is available (see, Bernard Binks (1998) Modern Aspects of Emulsion Science, Royal Society of Chemistry, Cambridge, UK; Petersen and Hamill (1968) J. Soc. Cosmetic Chemists. 19:627-640; Leal-Calderon, Thivilliers (2007) Curr. Opinion in Colloid and Interface Science. 12:206-212). Methods and devices for measuring, e.g., viscosity of emulsions are available (see, Sherman (1962) The viscosity of emulsions. Rheologica Acta. 2:74-82; Farah, Oliveira, Caldas (2005) J. Petroleum Science and Engineering. 48:169-184). Methods and devices for measuring, e.g., turbidity and stability of emulsions are available (see, Zhang and Reineccius (2016) LWT—Food Science and Technology 71:162-168; Iqbal, Baloch, Hameed (2014) J. Chem. Soc. Pak. 36:204-210).

Non-Ethanol Solvents.

The system, reagents, compositions, emulsions, extracts, reagents, fluids, and methods, of the present disclosure comprise a non-ethanol solvent, or a mixture of at least two different non-ethanol solvents, or a mixture of two or more non-ethanol solvents plus in addition ethanol, or a mixture of one non-ethanol solvent plus water, or a mixture of two or more non-ethanol solvents plus in addition water. Non-ethanol solvents can be, for example, acetic acid, acetone, acetonitrile, anisole, benzene, 1-butanol, 2-butanol, butylacetate, tert-butylmethylether, carbon tetrachloride, chlorobenzene, chloroform, cumene, cyclohexane, 1,2-dichlorethane, 1,1-dichloroethene, 1,2-dichloroethene, 1,2-methoxyethane, dichloromethane, N,N-dimethylacetamide (DMA), N,N-dimethylformamide (DMF), dimethylsulfoxide (DMSO), 1,4-dioxane, 2-ethoxyethanol, ethylacetate, ethyleneglycol, ethylether, ethylformate, formamide, formic acid, heptane, hexane, isobutylacetate, isopropylacetate, methanol, 2-methoxyethanol, methylacetate, 3-methyl-1-butanol, methyl-butyl-ketone ($CH_3(CH_2)_3COCH_3$), methylcyclohexane, methylethylketone, methylisobutylketone, 2-methyl-1-propanol, N-methyl-pyrrolidone, nitromethane, nitromethane, pentane, 1-pentanol, 1-propanol, 2-propanol, pyridine, propylacetate, pyridine, sulfolane, tetrahydrofuran (THF), tetralin, toluene, 1,1,1-trichlorethane, 1,1,2-trichloroethene, triethylamine, xylene, and so on. The disclosure encompasses fluorettes.

In embodiments, the system, compositions, extracts, reagents, solutions, fluids, liquids, and methods of the present disclosure, can encompass any composition, extract, reagent, solution, fluid, or liquid, that comprises about 2%, about 4%, about 6%, about 8%, about 10%, about 12%, about 14%, about 16%, about 18%, about 20%, about 25%, about 30%, about 35%, about 40%, about 45%, or about 50% of any one of the above non-ethanol solvents.

Exclusionary Embodiments Relating to Solvents.

In exclusionary embodiments, the system, compositions, extracts, reagents, solutions, fluids, liquids, and methods of the present disclosure, can exclude any composition, extract, reagent, solution, fluid, or liquid, that contains any one of the above non-ethanol solvents, that contains over 1% of any one of the above non-ethanol solvents, that contains over 2% of any one of the above non-ethanol solvents, that contains over 4%, over 6%, over 8%, over 10%, over 12%, over 14%, over 16%, over 18%, or over 20% of any one of the above non-ethanol solvents.

In other exclusionary embodiments, the system, compositions, extracts, reagents, solutions, fluids, liquids, and methods of the present disclosure, can exclude any composition, extract, reagent, solution, fluid, or liquid, that contains any one of the above non-ethanol solvents, that contains about 1% of any one of the above non-ethanol solvents, that contains about 2% of any one of the above non-ethanol solvents, or that contains about 4%, about 6%, about 8%, about 10%, about 12%, about 14%, about 16%, about 18%, or about 20% of any one of the above non-ethanol solvents.

Exclusionary Embodiments (Chemical Engineering)

In embodiments, the system, devices, structures, compositions, extracts, reagents, solutions, fluids, liquids, and methods of the present disclosure, can exclude any system, device, or method, that involves "distilling an organic oil," that involves "distilling an organic oil where the distilling comprises vacuum distillation," that involves "vaporizing an organic oil," that comprises, "vaporizing an organic oil where the organic oil was extracted from plant matter," that involves "recycling a solvent where this solvent is reused to extract plant matter," that involves "recycling a solvent where this solvent is reused to extract plant matter (where this plant matter has already been extracted at least once)," that involves "recycling a solvent where this solvent is reused to extract plant matter (plant matter than has never before been extracted)," that involves "evaporating a solvent but without recovery of the solvent (recovering this solvent after it has been evaporated)." In other exclusionary embodiments, the system, devices, structures, compositions, extracts, reagents, solutions, fluids, liquids, and methods of the present disclosure, can exclude any system, device, or method, that has an "oil container where extracted oils are collected" and a "cooling chamber" but where the "oil container" and the "cooling chamber" do not occur in the same "environmental box" or do not occur in the same enclosure that is maintained at a cool temperature (that is, that is maintained at a temperature that is at least 5 degrees C., at least 10 degrees C., at least 15 degrees C., at least 20 degrees C., or at least 30 degrees C., or at least 40 degrees C., or at least 50 degrees C., below room temperature (23 degrees C.)).

Exclusionary Embodiments Relating to Filters

In other exclusionary embodiments relating to chemical engineering, the present disclosure can exclude any system, device, or method, that has a "filter" (or filter assembly, or filter stack, or filtration stack, or inline filter strainer) that is capable of filtering plant extracts, or that is capable of filtering emulsions acquired by extracting plant matter, wherein the "filter" (or filter assembly, or filter stack, or filtration stack, or inline filter strainer) is not in the same cooled compartment (for example, not in the same "environmental box") as one or more or all of: (i) Solvent storage tank; (ii) Extraction tank used for extracting plant matter; (iii) Pipes or tubes that are used for recycling a plant extract back into extraction tank for effecting further extraction of plant matter that has already been extracted at least once, (iv) Vessel that serves as an intermittent storage ballast for extract-rich emulsions.

FIG. 1 shows the use of an extraction apparatus designed to perform extraction in accordance with the present invention.

Steps 1 and 2 of the process represent a pre-process step in which both the solvent and plant substrate are chilled to a desired temperature between –1 C and —SOC, preferably to a temperature between –30 C and –50 C, ideally to a temperature range between –40 C and –45 C. In this embodiment of the aforementioned step, the use of an ultra-low freezer is adequate. In another embodiment of Step 1 the solvent can be chilled via jacketed extraction vessel and cryo chiller assembly. This step requires a long period of time to achieve the desire temperature of the solvent, and therefore it is recommended that an ultra-low storage freezer is acquired to prevent a bottle necking at Step 1 or 2.

Step 3 includes a jacketed extraction vessel such as a chemical reactor. In another embodiment of Step 3 of a jacketed collection vessel, such as a chemical reactor can be added to the apparatus. In this embodiment, the jacketed collection vessel allows to create a re-circulating system to move chilled solvent from collection vessel back into the extraction vessel. Re-circulating chilled solvent over the plant substrate, has been recognized to produce a richer concentration of desired essential oils, cannabinoids, flavonoids and terpenes in the concentrate emulsion. In a third embodiment of Step 3 a jacketed holding vessel, such as a chemical reactor, can be added to the apparatus assembly. In this embodiment the holding vessel allows for mechanical feeding of the solvent into the extraction vessel, eliminating strenuous manual labor of pouring solvent into the extraction vessel by hand. In all embodiments of Step 3 the vessels must be able to maintain a desired temperature range of –40 C to –45 C. A cryo chiller has been recognized as an effective device to chill the extraction apparatus by circulating a cooling solution throughout the jackets of the vessel included in the apparatus assembly. Step 4a includes a process in which the chilled solvent is transferred into the collection vessel. Step 1 of FIG. 2 allows for the solvent to be chilled within the vessel via circulation of cooling solution within the jacket walls of the vessel. Step 4b includes a process in which the plant substrate is placed inside the extraction vessel of the apparatus. In one embodiment the plant substrate can be loosely placed inside the extraction vessel. In another embodiment the extraction vessel is lined with a micron mesh screen bag prior to the introduction of the plant substrate into the vessel. Lining the extraction vessel with a micron screen bag allows for immediate separation of concentrate emulsion and plant substrate during the concentrate emulsion evacuation of Steps 6a and 6b. This method also allows for the quick evacuation of plant substrate from the extraction vessel by simply removing the bag filled with plant substrate out of the vessel.

Step 5 allows for contact time between chilled solvent and chilled plant substrate. The contact period should be carried out at the ideal temperature range between –40 C and –45 C. Contact time can be between 1 minute and 60 minutes, preferably between 3 minutes and 10 minutes, ideally between 1 minute and 5 minutes.

Step 7 includes a process of inline separation of concentrate emulsion and plant substrate. An embodiment Step 4b of FIG. 2 provides that plant substrate is placed within a micron mesh bag prior to its introduction into the extraction vessel. This embodiment of Step 4b has been recognized as the most simple and cost effective way of inline filtration. In another embodiment of Step 7, a solid stainless steel micron screen can be introduced via a false bottom inside the extraction vessel. In this embodiment of Step 7, the plant substrate sits atop the false bottom stainless micron mesh as the concentrate emulsion is drawn through it and out of the extraction vessel. In a third embodiment of Step 7 a filter holder can be introduced in line between the extraction vessel and collection vessel into the apparatus assembly.

Step 8 of FIG. 2 includes the collection of concentrate emulsion from the extraction vessel into a jacketed collection vessel referenced in embodiments of Step 3.

Step 9a includes a process of recirculation of concentrate emulsion back over the plant substrate to create a richer concentration of desired constituents of the plant substrate. Recirculation can be performed via mechanical solvent pump, positive pressure in collection vessel, or negative pressure within extraction vessel. The preferred method for recirculation is by manipulating pressure within the vessels. Moving the concentrate emulsion from vessel to vessel via negative pressure has proven to be the most cost effective as vacuum pumps have a long life expectancy and do not require much maintenance. Pressurizing the vessels to move the concentrate emulsion has also been recognized as effective, but the added expense of food grade nitrogen or expensive moisture traps and filters for ambient air compressors have proven to be burdensome. Mechanical solvent pumps have been recognized as an effective means of moving the solvent and concentrate emulsion, but the costs associated with such devices would deter small operators from applying this method.

Step 9b includes a method for evacuating the concentrate emulsion from the collection vessel. As referenced in Step 9a, moving the solvent or concentrate emulsion can be achieved via positive or negative pressure within the vessels of the apparatus. For evacuation, it is been discovered that a simple drain at the bottom vessel is suitable for evacuation of the concentrate emulsion. Positive pressure can be applied to the collection vessel to expedite the evacuation process.

Step 10 provides a method for separating the concentrate from solvent via rotary evaporator, simple distillation, or atmospheric evaporation. The preferred method is rotary evaporator as this method allows for recovery of the solvent in its entirety. The recovered solvent is put back into circulation for future extraction, making this method one of the most cost effective for any processor.

According to another embodiment of the system, other features are taught. In another embodiment of the present invention, a system comprising of jacketed reactor extraction vessel, jacketed reactor collection vessel, plumbing, valves, hoses, ultra low circulating chiller, vacuum pump, liquid nitrogen holding Dewar, pressure regulators, LN2 phase separators, pneumatic actuators, electronic relay switches and air compressor. In this embodiment, the system is scaled for larger throughput, with vessels capable of holding up to 20 LBS of plant material and up to 40 gallons of solvent.

In this embodiment of the present invention, an ultra-low circulating chiller is attached to the jackets on the reactor vessels.

The ultra-low recirculating chiller is set to the desired temperature set point of −75 C and allowed time to chill the internal chamber of the reactor vessels. The vessels are interconnected via sanitary plumbing, pneumatic actuated valves in a manner which allows for the transfer of solvent into the extraction tank, and the recollection of the extract rich emulsion produced during extraction back into the collection vessel.

In this embodiment, the collection vessel acts as the solvent storage vessels prior to commencing the extraction. During extraction procedure, the collection vessel acts as an intermittent emulsion storage vessel during recirculation procedures.

Plant material is loaded into a mesh screen bag and placed inside the extraction vessel. Allowing time for the material to chill to a desired temperature of below −35 C, preferably below −45 C, ideally below −55 C. Solvent is placed inside the collection and allowed time to chill to the necessary temperature range between −45 and −75 C. It has been discovered that the ideal extraction temperature is in the range of −45 C and −50 C system parameters are always set to a lower temperature to compensate for the heating of solvent and material during fluid transfers. The solvent will typically gain 5 degrees during each fluid transfer. A typical recirculation procedure requires the solvent to be moved up to 5 times from extraction vessel to collection vessel and back. This raises the overall temperature of the solvent in the system by up to 25 degrees Celsius.

In another embodiment of the present invention, a solvent transfer pump can be employed to move solvent from one vessel to the next, or to recirculate the emulsion within the extraction vessel. Mechanical pumps have shown to be efficient but tend to generate more heat the desired, therefore heating the solvent during fluid transfers or recirculation.

The method does not predictably work as desired in that lipids and chlorophyll become available to the solvent at temperatures above −40 C.

Without implying any limitation, the present disclosure provides compositions, reagents, devices, systems, and methods, that comprise one or more of the following solvents, for example, combinations of only two, of only three, of only four, of only five, of only six, or of more than six of the following solvents. The solvents are liquid carbon dioxide, supercritical carbon dioxide, ethanol in water, ethanol in a solvent that is not water, ethanol in a mixture of solvents where none are water, or ethanol in a solvent that is mixture of water plus another solvent that is not water. The solvents that are used with, or that are comprised by, the compositions, reagents, devices, systems, and methods of the present disclosure, can also include one or more of, any non-polar solvent, any mildly polar solvent, any highly polar solvent, butane, hexane, cyclohexane, ethane, pentane, octane, diethyl ether, methanol, ethanol, isopropanol, n-propanol, chloroform, ethyl acetate, acetone, diethylamine, xylene, dioxane or similar hydrocarbons or alcohols. Regarding the above-disclosed solvents (and also in the solvents disclosed below), unless specified otherwise, the list does not impose any limitation on which solvent is to be dissolved in which other solvent (or in which other of a plurality solvents).

The solvent, such as ethanol, can be chosen from the following concentrations, 0%, 0.01%, 1%, 5%, 10%, 15%, 20%, 25%, 30%, 35%, 40%, 45%, 50%, 55%, 60%, 65%, 70%, 75%, 80%, 85%, 90%, 95%, 99%, or 100% solvent (or the solvent can be in a range that is defined by any two of these percentages). In exclusionary embodiments, the compositions, reagents, devices, systems, and methods of the present disclosure can exclude any one or more of the above solvents, and can exclude any one or more of the above solvents at any one or more of the indicated percentage values.

The solvent, such as ethanol, can be chosen from one of the following concentrations: about 5%, about 10%, about 15%, about 20%, about 25%, about 30%, about 35%, about 40%, about 50%, about 60%, about 70%, about 75%, about 80%, about 85%, about 90%, about 95%, about 99.5%, about 100% solvent (or the solvent can be in a range that is defined by any two of these percentages). The term "about" can mean plus or minus 5%. The term "percent" means by volume. In exclusionary embodiments, the compositions, reagents, devices, systems, and methods of the present disclosure can exclude any one or more of the above solvents, and can exclude any one or more of the above solvents at any one or more of the indicated percentage values, and optionally, at the indicated "about" values.

The solvent, such as ethanol, can be chosen from the following concentrations, under 5%, under 10%, under 15%, under 20%, under 25%, under 30%, under 35%, under 40%, under 45%, under 50%, under 55%, under 60%, under 65%, under 70%, under 75%, under 80%, under 90%, under 95%, under 100% solvent. The percentage value is preferably in terms of volume, but if necessary, the percentage value can be expressed in terms of weight. The volumes or weights are preferably measured at room temperature (23 degree C.), where the prepared solvent is then adjusted to a desired temperature, such as to minus 30 degrees C. or to minus 50 degrees C. Regarding the above list, the present disclosure encompasses each of the above solvents in an "about" embodiments.

The solvent, such as ethanol, can be chosen from the following concentrations: Concentrations that are over 5%, over 10%, over 15%, over 20%, over 25%, over 30%, over 35%, over 40%, over 45%, over 50%, over 55%, over 60%, over 65%, over 70%, over 75%, over 80%, over 85%, over 90%, over 95% solvent, or over 99%. Regarding the above list, the present disclosure encompasses each of the above solvents in an "about" embodiments. In exclusionary embodiments, the compositions, reagents, devices, systems, and methods of the present disclosure can exclude any one or more of the above solvents, and can exclude any one or more of the above solvents at the indicated percentage values, and at the indicated "about" values.

In "consisting" embodiments, what is provided is a solvent that consists of 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. The ethanol can be grain alcohol. Regarding the above list, the present disclosure encompasses each of the above solvents in an "about" embodiments.

In exclusionary embodiments, the present disclosure can exclude any system, device, composition, solution, or method, that includes a solution (or that is a solution) that is 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. Regarding the above list, the present disclosure encompasses each of the above solvents in an "about" embodiments.

In exclusionary embodiments, the present disclosure can exclude any system, device, composition, solution, or method, that includes a solution (or that is a solution) that has a percentage value of ethanol that is less than 100% ethanol, less than 98% ethanol, less than 95% ethanol, less than 90% ethanol, less than 85% ethanol, less than 80% ethanol, less than 75% ethanol, less than 70% ethanol, less than 65% ethanol, less than 60% water, and the like. The ethanol can be grain alcohol. In this list, the liquid that is not ethanol can be water, pure water, distilled water, acetone, hexane, butane, or any solvent that is not water. Also, in this list, the liquid that is not ethanol can be a single kind of solvent, such as only water, or only acetone, or only hexane, or only butane. Also, in this list, the liquid that is not ethanol can be a mixture of two or more other solvents where none of them are water. Moreover, in this list, the liquid that is not ethanol can be a mixture of two or more other solvents where one of them is water.

Regarding the above list, the present disclosure encompasses each of the above solvents in an "about" embodiments. An "about" embodiment, to give an example, is: a solvent that consists of about 90% ethanol with about 10% water." The sum of the percentage of ethanol and the percentage of water is 100%. This value of 100% can refer to a solvent composition (or solvent mixture) that is used by itself. Alternatively, this value of 100% can refer to a solvent composition (or solvent mixture) that is used as a component with one or more additional solvents, as in the example of the combination of a first solvent solution that is 95% ethanol with 5% water plus a second solvent solution that consists of 100% acetone (for this example, the relative volumes of the first solvent solution are not and of the second solvent solution are not given).

In "comprising" embodiments, what is provided is a solvent that comprises 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. The use of the word "comprising" means that the system can include the solvent mixtures that include more than just two chemicals (the two chemicals, water and ethanol). The use of the "comprising" language means that, to give an example, a "solvent" can consist of a mixture of a first solvent that is ten milliliters of "100% acetone" and a second solvent that is 250 milliliters of "95% ethanol with 5% water." Regarding the above list, the present disclosure encompasses each of the above solvents in an "about" embodiments. An "about" embodiment, to give an example, is: a solvent that comprises about 90% ethanol with about 10% water."

In a preferred embodiment, a solvent (such as ethanol) is dissolved in only one solvent, where this one solvent is water. In another embodiment, a solvent (such as ethanol) is dissolved in a mixture of only two other solvents. In yet another embodiment, a solvent (such as ethanol) is dissolved in a mixture of only three solvents. In still another embodiment, a solvent (such as ethanol) is dissolved in a mixture of one or more additional solvents, or dissolved in mixture of two or more additional solvents, or dissolved in a mixture of three or more additional solvents. Also, in another embodiment, the solvent (such as ethanol) can be dissolved in a mixture of a plurality of solvents, where one of these is water. Also, the solvent (such as ethanol) can be dissolved in a mixture of a plurality of solvents, where none of these is water. The term "about" preferably means plus or minus 5%. In other embodiments, the term "about" can mean plus or minus 1%, plus or minus 2%, plus or minus 6%, or plus or minus 8%. The term "percent" means by volume. Regarding the above-disclosed solvents, unless specified otherwise, the list does not impose any limitation on which solvent is to be dissolved in which other solvent (or in which plurality of other solvents). In exclusionary embodiments, the compositions, reagents, devices, systems, and methods of the present disclosure can exclude any one or more of the above solvents, and can exclude any one or more of the above solvents at the indicated percentage values, and at the indicated "about" values.

The present disclosure provides compositions, reagents, devices, systems, and methods, that comprise one or more polar solvents, one or more non-polar solvents, or that comprise one or more of each of polar and non-polar solvents. Polar solvents have large dipole moments, also known as, "partial charges." They contain bonds between atoms with very different electronegativities, such as oxygen and hydrogen. Non-polar solvents contain bonds between atoms with similar electronegativities, such as carbon and hydrogen, such as octane. Bonds between atoms with similar electronegativities will lack partial charges. This absence of charge which makes these molecules "non-polar." Polarity can be measured by two direct ways. One is through measuring a constant called "dielectric constant." The greater the dielectric constant, the greater the polarity (value for water is high, value for gasoline is low). A second way comes from directly measuring the dipole moment. Polarity is a continuum. While pentane is "non-polar" and water is "polar", there are borderline cases such as diethyl ether, dichloromethane, and tetrahydrofuran (THF) which have both polar and non-polar characteristics. A dividing line between "polar" and "non-polar" is miscibility with water. Diethyl ether and dichloromethane do not mix with water. On the other hand, THF, DMSO, acetonitrile, DMF, acetone and short-chain alcohols do (see, Ashenhurst, James. Substitution Reactions. Masterorganicchemistry dot com). For several nonpolar solvents, the dielectric constants are as follows: pentane (1.8), hexane (1.9), cyclohexane (2.0), benzene (2.4), toluene (2.3), chloroform (4.8), diethylether (4.3). For several polar solvents, the dielectric constants are as follows: acetone (21), demethylformamide (38), acetonitrile (37), ammonia (25), t-butanol (12), ethanol (25) methanol (33), acetic acid (6.2), water (80). The dielectric constants of glycerol (45), ethanol (25), and water (80), and dependence on temperature, are disclosed in, Ponomarenko, Yang, Katsnelson (2009) Effect of high-kappa environment on charge carrier mobility in graphene. Physical Review Letters. 102:206603. The dielectric constrant of acetone (20.7) is disclosed by Goto, Kawata, Nakamura, Aoyama (1986) J. Microencapsulation. Vol. 3, Issue 4. In embodiments, the present disclosure provides compositions, reagents, devices, systems, and methods, can include one or more of the above solvents, such as about 20% acetone, about 30% acetone, about 40% acetone, about 50% acetone, about 60% acetone, about 70% acetone, about 80% acetone, about 90% acetone, or about 95% acetone dissolved in a solvent that is water, or 100% acetone. The term "about" can mean plus or minus 5%. The term "percent" means by volume. Regarding the above-disclosed solvents, unless specified otherwise, the list does not impose any limitation on which solvent is to be dissolved in which other solvent (or in which other solvents). In exclusionary embodiments, the compositions, reagents, devices, systems, and methods of the present disclosure can exclude any one or more of the above solvents, and can exclude any one or more of the above solvents at the indicated percentage values, and at the indicated "about" values.

"Essentially Of" Solvent Embodiments.

The present disclosure provides a solvent consisting essentially of heptane, or consisting essentially of hexane, or consisting essentially of isopropyl alcohol, or consisting essentially of methanol. Alternatively, or in addition, the present disclosure provides a solvent consisting of at least 99% heptane, or consisting of at least 99% hexane, or consisting of at least 99% isopropyl alcohol, or consisting of at least 99% methanol, where the percentage can be in units of weight when measured at room temperature (about 23 degrees C.) or in units of volume when measured at room temperature (about 23 degrees C.). The remaining one percent (1%) can take the form, for example, of a solute or solutes, or suspended particles, or some other type of solvent, or of an insoluble fluid.

Alternatively, or in addition, the present disclosure provides a solvent consisting of at least 95% heptane, or consisting of at least 95% hexane, or consisting of at least 95% isopropyl alcohol, or consisting of at least 95% methanol. The remaining five percent (5%) can take the form, for example, of a solute or solutes, or suspended particles, or some other type of solvent, or of an insoluble fluid.

"Safer Extraction Process" Embodiments.

Safer, or "safer and more reliable" extraction process embodiments encompass, without implying any limitation, an extraction process where there is reduced risk of a fire, for example, a fire that can be initiated by an electric spark, or by a freshly extinguished match where the match head is still hot, or by a burning match, or by a flame such as that from a Bunsen burner. "Safer and more reliable" can also encompass reduced exposure of workers to solvents and, for example, reduced risk of lung damage, skin damage, or eye damage. Guidance on assessing damage to organs and tissues is provided by, e.g., Norgaard, Hansen, Sorli (2014) Toxicol. Sci. 137:179-188, Aytacoglu, Calikoglu, Tamer (2006) Respiration. 73:100-104; Emre, Aktay, Polat (2007) Chin. J. Physiol. 50:143-144; Tanios, El Gamal, Rosenburg (2004) Respiration. 71:642-645 Johnson (2004) Int. J. Toxicol. 23 (Suppl.1) 29-57).

Evaporation Embodiments.

One standard atmosphere equals 760 mm mercury (Hg). This is equivalent to 760 Torr (see, Fradette, R. J., Jones, W. R., and Jones, T. (2016) Understanding Vacuum Measurement. Solar Atmospheres, Inc., Souderton, Pa.). The system, device, reagents, and methods of the present disclosure can be exposed to conditions that promote evaporation, where the conditions are atmosphere at 760 Torr (not under pressure, and not under vacuum), or atmosphere at between 760 and 700 Torr, or 700-650 Torr, or 650-600 Torr, or 600-550 Torr, or 550-500 Torr, or 500-450 Torr, or 450-400 Torr, or 400-350 Torr, or 350-300 Torr, or 300-250 Torr, or 250-200 Torr, or 200-150 Torr, or 150-100 Torr, or 100-50 Torr, or 50-40 Torr, or 40-30 Torr, or 30-20 Torr, or 20-15 Torr, or 15-10 Torr, or 10-5 Torr, or 5-1.0 Torr, or 1.0-0.1 Torr, or 0.1-0.01 Torr, or 0.01-0.001 Torr, or 0.001-0.0001 Torr, or to a range that is under 760 Torr, under 700 Torr, or under 650 Torr, or under 600 Torr, or under 550 Torr. or under 500 Torr, or under 450 Torr, or under 400 Torr, or under 350 Torr, or under 300 Torr, or under 250 Torr, or under 200 Torr, or under 150 Torr, or under 100 Torr, or under 50 Torr, or under 25 Torr, or under 10 Torr, or under 5 Torr, or under 1.0 Torr, or under 0.1 Torr, or under 0.01 Torr, and so on. In exclusionary embodiments, the present disclosure can exclude any system, device, reagent, composition, or method, that involves exposure or that is exposed to one or more of the above vacuum ranges.

Further regarding evaporation embodiments, the present disclosure encompasses systems, devices, compositions, reagents, and methods, where the rate of evaporation (for example, evaporation of a solvent from an emulsion, or evaporation of a solvent from a solution, or the rate of evaporation of a two or more different kinds of solvents from an emulsion or a solution), is enhanced for example by the passage of air over the top of the solution or emulsion, or by the passage of air through the solution or emulsion (e.g., by bubbling), or by a combination of passage over the top and through the solution or emulsion. In embodiments, the rate of passage is about one cubic centimeter (cm) of air per second over a surface area of one square cm, or it can be a rate of passage of about one cubic centimeter of air per second being bubbled through a one liter volume of solution or emulsion. Alternatively, instead of "one cubic centimeter of air," as recited above, the value can be about 0.001, 0.01, 0.1, 2, 4, 6, 8, 10, 15, 20, 30, 40, 50, 60, 80, 100, 150, 200, 250, 300, 350, 400, or more cubic centimeters of air (either over the surface or being bubbled through the one liter volume) per second. Values of passage can be "about" embodiments of any of the recited values, or can take the form of a range created by any two of the above values, and the like. Passage of air can be driven by a vacuum or, alternatively, passage of air can be driven by pressure or, alternatively, by a combination of pressure and vacuum. The air can be atmospheric air or, alternatively, it can take the form of a gas that is about 20%, about 30%, bout 40%, about 50%, about 60%, about 70%, about 80%, about 90%, about 95%, about 98%, or about 100% nitrogen (or of some other gas).

In exclusionary embodiments, the present disclosure can exclude any system, device, reagent, composition, or method, that uses or that is exposed to one of the above "passage of air" embodiments.

Temperature embodiments.

In temperature embodiments, the present disclosure provides compositions, reagents, devices, systems, and methods, that include one or more solvents, such as any of the solvents that are disclosed in the above paragraphs, or in any of the following paragraphs, where the temperature (Centigrade) is 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. What is also provided is a solvent with a temperature that is in a range defined by any of the above two temperatures, such as the range of minus 30 degrees to minus 50 degrees. In exclusionary embodiments, the present disclosure can exclude any solvent that has one of the above temperatures, or it can exclude any composition, reagent, device, system, or method that comprises a solvent having one of the above temperatures.

Also, what is provided is a solvent that has a temperature (Centigrade) of about 20 degrees, about 15 degrees, about 10 degrees, about 5 degrees, about 0 degrees, about minus 5 degrees, about minus 10 degrees, about minus 15 degrees, about minus 20 degrees, about minus 25 degrees, about minus 30 degrees, about minus 35 degrees, about minus 40 degrees, about minus 45 degrees, about minus 50 degrees, about minus 55 degrees, about minus 60 degrees, about minus 65 degrees, about minus 70 degrees, about minus 75 degrees, or about minus 80 degrees. What is also provided is a solvent that has a temperature that is in a range defined by any of the above two temperatures, such as the range of about minus 30 degrees to about minus 50 degrees. The term "about" can mean plus or minus 5 degrees. In exclusionary embodiments, the present disclosure can exclude any solvent that has one of the above temperatures, or it can exclude any composition, reagent, device, system, or method that comprises a solvent that has one of the above temperatures.

In "greater than" embodiments, the present disclosure provides compositions, reagents, devices, systems, and methods, that include one or more solvents, such as any of the above-disclosed solvents has a temperature that is "greater than" 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. "About" embodiments of these "greater than" ranges are also provided by the present disclosure, where "about" means plus or minus five degrees.

In "lesser than" embodiments, the present disclosure provides compositions, reagents, devices, systems, and methods, that include one or more solvents, such as any of the above-disclosed solvents has a temperature that is "lesser than" 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. "About" embodiments of these "lesser than" ranges are also provided by the present disclosure, where "about" means plus or minus five degrees.

Without implying any limitation, in embodiments the present disclosure also encompasses "about" embodiments. Where the word "about" occurs in a claim as originally filed, or where the word "about" is added to a claim by way of amendment, the meaning of the word "about" can be caused to be more precisely defined by way of an amendment that adds one or more of the following limitation to the claim. The word "about" can mean, plus or minus 5%, plus or minus 10%, plus or minus 15%, plus or minus 20%, plus or minus 25%, plus or minus 30%, and so on. Also, the word "about" can mean that a given number that exists in a series of numbers (where the claim includes the word, about) encompasses all values that are between the previous number in the series and the subsequent number in the series. Similarly, the word "about" can mean that a given number in a series of numbers (where the claim includes the word, about) encompasses all values that are half-way and less than half-way in between that number and the immediately previous number in that series, and also encompasses all values that are half-way and less than half-way in between that number and the immediately subsequent number in that series.

In range embodiments, the system, device, compositions, solutions, and methods of the present disclosure encompass a solvent or a solution or a mixture of solvents, that is in one of the following temperature ranges (minus degrees C.): 10-15; 10-20; 10-25; 10-30; 10-35; 10-40; 10-45; 10-50; 10-55; 10-60; 10-65; 10-70; 10-75; 10-80; or 10 to lesser than 80 degrees C. Other temperature ranges (minus degrees C.): 20-25; 20-30; 20-35; 20-40; 20-45; 20-50; 20-55; 20-60; 20-65; 20-70; 20-75; 20-80; or 20 to lesser than 80 degrees C. Even more temperature ranges (minus degrees C.): 25-30; 25-35; 25-40; 25-45; 25-50; 25-55; 25-60; 25-65; 25-70; 25-75; 25-80; or 25 to lesser than 80 degrees C. Still further temperature ranges (minus degrees C.): 30-35; 30-40; 30-45; 30-50; 30-55; 30-60; 30-65; 30-70; 30-75; 30-80; or 30 to lesser than 80 degrees C. And more temperature ranges (minus degrees C.): 35-40; 35-45; 35-50; 35-55; 35-60; 35-65; 35-70; 35-75; 35-80; or 35 to lesser than 80 degrees C. Yet more temperature ranges (minus degrees C.): 40-45; 40-50; 40-55; 40-60; 40-65; 40-70; 40-75; 40-80; or 40 to lesser than 80 degrees C.

In exclusionary embodiment, the present disclosure can exclude any system, device, solution, solvent, mixture of solvents, and method, that is at a temperature within any of the above temperature ranges.

In substance impurity embodiments, the present disclosure can result in a solution, emulsion, composition, slurry, extract, extraction, oil, aqueous solution, where the percentage of a "substance impurity" (percentage by weight within the solution, or emulsion, or extract, etc.) is less than 10% of the total weight, less than 8%, less than 6%, less than 5%, less than 4%, less than 3%, less than 2%, less than 1%, less than 0.8%, less than 0.6%, less than 0.4%, less than 0.2%, less than 0.1%, less than 0.08%, less than 0.06%, less than 0.04%, less than 0.02%, less than 0.01%, less than 0.008%, less than 0.006%, less than 0.004%, less than 0.002%, less than 0.001% of the total weight, and the like. The "substance impurity" can be a substance that is "total pigments," or it can be "chlorophyll," or it can be "total lipids," or it can be the sum of chlorophyll plus waxes, or it can be "waxes," or it can be synthetic pesticides, or the "substance impurity" can refer to the sum of all pigments, lipids, waxes, and synthetic pesticides, and degradants of synthetic pesticides. The skilled artisan understands that the word "pigment" usually means a substance that, to the human eye, has a color such as red, orange, yellow, green, blue, and so on, when present for example at a concentration of about 0.05% in a solution, or at a concentration of about 1.0% in a solution or at a concentration of about 5.0% in a solution.

Solvents, Mixtures of Solvents, and Percentages.

Without implying any limitation, the present disclosure provides compositions, reagents, devices, systems, and methods, that comprise one or more of the following solvents, for example, combinations of only two, of only three, of only four, of only five, of only six, or of more than six of the following solvents. The solvents are liquid carbon dioxide, supercritical carbon dioxide, ethanol in water, ethanol in a solvent that is not water, ethanol in a mixture of solvents where none are water, or ethanol in a solvent that is mixture of water plus another solvent that is not water. The solvents that are used with, or that are comprised by, the compositions, reagents, devices, systems, and methods of the present disclosure, can also include one or more of, any non-polar solvent, any mildly polar solvent, any highly polar solvent, ethane, propane, butane, pentane, hexane, cyclohexane, octane, nonane, decane, undecane, dodecane, diethyl ether, methanol, ethanol, isopropanol, isopropyl alcohol, n-propanol, chloroform, ethyl acetate, acetone, diethylamine, xylene, dioxane or similar hydrocarbons or alcohols. Regarding the above-disclosed solvents (and also in the solvents disclosed below), unless specified otherwise, the list does not impose any limitation on which solvent is to be dissolved in which other solvent (or in which other of a plurality solvents).

The solvent, such as ethanol, can be chosen from the following concentrations, 0%, 0.01%, 1%, 5%, 10%, 15%, 20%, 25%, 30%, 35%, 40%, 45%, 50%, 55%, 60%, 65%, 70%, 75%, 80%, 85%, 90%, 95%, 99%, or 100% solvent (or the solvent can be in a range that is defined by any two of these percentages). In exclusionary embodiments, the compositions, reagents, devices, systems, and methods of the present disclosure can exclude any one or more of the above solvents, and can exclude any one or more of the above solvents at any one or more of the indicated percentage values.

The disclosure provides solvents (a solvent composition) comprising ethane at any of the above concentrations, where the solution also contains water to bring sum of the percent ethane plus percent water to equal 100%. In exclusionary embodiments, the present disclosure can exclude any system, device, composition, solution, extract, and method, that comprises the above solvent composition.

Also, the disclosure provides solvents (a solvent composition) consisting of ethane at any of the above concentrations, where the solution also contains one or more solvents (none of which is water) to bring sum of the percent ethane plus percent "one or more solvents, none of which is water," to equal 100%. In exclusionary embodiments, the present disclosure can exclude any system, device, composition, solution, extract, and method, that comprises the above solvent composition.

Moreover, the disclosure provides solvents (a solvent composition) consisting of ethane at any of the above concentrations, where the solution also contains two or more solvents (at least one being a solvent that is not water, and where one of the solvents is water) to bring sum of the percent ethane plus all of the other solvents to equal 100%. In exclusionary embodiments, the present disclosure can exclude any system, device, composition, solution, extract, and method, that comprises the above solvent composition.

The solvent, such as ethanol, can be chosen from one of the following concentrations: about 5%, about 10%, about 15%, about 20%, about 25%, about 30%, about 35%, about 40%, about 50%, about 60%/o, about 70%, about 75%, about 80%, about 85%, about 90%, about 95%, about 99.5%, about 100% solvent (or the solvent can be in a range that is defined by any two of these percentages). The term "about" can mean plus or minus 5%. The term "percent" means by volume. In exclusionary embodiments, the compositions, reagents, devices, systems, and methods of the present disclosure can exclude any one or more of the above solvents, and can exclude any one or more of the above solvents at any one or more of the indicated percentage values, and optionally, at the indicated "about" values.

The solvent, such as ethanol, can be chosen from the following concentrations, under 5%, under 10%, under 15%, under 20%, under 25%, under 30%, under 35%, under 40%, under 45%, under 50%, under 55%, under 60%, under 65%, under 70%/i, under 75%, under 80%, under 90%, under 95%, under 100% solvent. The percentage value is preferably in terms of volume, but if necessary, the percentage value can be expressed in terms of weight. The volumes or weights are preferably measured at room temperature (23 degree C.), where the prepared solvent is then adjusted to a desired temperature, such as to minus 30 degrees C. or to minus 50 degrees C. Regarding the above list, the present disclosure encompasses each of the above solvents in an "about" embodiments.

The solvent, such as ethanol, can be chosen from the following concentrations: Concentrations that are over 5%, over 10%, over 15%, over 20%, over 25%, over 30%, over 35%, over 40%, over 45%, over 50%, over 55%, over 60%, over 65%, over 70%, over 75%, over 80%, over 85%, over 90%, over 95% solvent, or over 99%. Regarding the above list, the present disclosure encompasses each of the above solvents in an "about" embodiments. In exclusionary embodiments, the compositions, reagents, devices, systems, and methods of the present disclosure can exclude any one or more of the above solvents, and can exclude any one or more of the above solvents at the indicated percentage values, and at the indicated "about" values.

In "consisting" embodiments, what is provided is a solvent that consists of 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. The ethanol can be grain alcohol. Regarding the above list, the present disclosure encompasses each of the above solvents in an "about" embodiments.

In exclusionary embodiments, the present disclosure can exclude any system, device, composition, solution, or method, that includes a solution (or that is a solution) that is 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. Regarding the above list, the present disclosure encompasses each of the above solvents in an "about" embodiments.

In exclusionary embodiments, the present disclosure can exclude any system, device, composition, solution, or method, that includes a solution (or that is a solution) that has a percentage value of ethanol that is less than 100% ethanol, less than 98% ethanol, less than 95% ethanol, less than 90% ethanol, less than 85% ethanol, less than 80% ethanol, less than 75% ethanol, less than 70% ethanol, less than 65% ethanol, less than 60% water, and the like. The ethanol can be grain alcohol. In this list, the liquid that is not ethanol can be water, pure water, distilled water, acetone, hexane, butane, or any solvent that is not water. Also, in this list, the liquid that is not ethanol can be a single kind of solvent, such as only water, or only acetone, or only hexane, or only butane. Also, in this list, the liquid that is not ethanol can be a mixture of two or more other solvents where none of them are water. Moreover, in this list, the liquid that is not ethanol can be a mixture of two or more other solvents where one of them is water.

Regarding the above list, the present disclosure encompasses each of the above solvents in an "about" embodiments. An "about" embodiment, to give an example, is: a solvent that consists of about 90% ethanol with about 10% water." The sum of the percentage of ethanol and the percentage of water is 100%. This value of 100% can refer to a solvent composition (or solvent mixture) that is used by itself. Alternatively, this value of 100% can refer to a solvent composition (or solvent mixture) that is used as a component with one or more additional solvents, as in the example of the combination of a first solvent solution that is 95% ethanol with 5% water plus a second solvent solution that consists of 100% acetone (for this example, the relative volumes of the first solvent solution are not and of the second solvent solution are not given).

In "comprising" embodiments, what is provided is a solvent that comprises 100% ethanol or 100% grain alcohol, 98% ethanol with 2% water, 95% ethanol with 5% water, 90% ethanol with 10% water, 85% ethanol with 15% water, 80% ethanol with 20% water, 75% ethanol with 25% water, 70% ethanol with 30% water, 65% ethanol with 35% water, 60% water with 40% water, and the like. The use of the word "comprising" means that the system can include the solvent mixtures that include more than just two chemicals (the two chemicals, water and ethanol). The use of the "comprising" language means that, to give an example, a "solvent" can consist of a mixture of a first solvent that is ten milliliters of "100% acetone" and a second solvent that is 250 milliliters of "95% ethanol with 5% water." Regarding the above list, the present disclosure encompasses each of the above solvents in an "about" embodiments. An "about" embodiment, to give an example, is: a solvent that comprises about 90% ethanol with about 10% water."

In a preferred embodiment, a solvent (such as ethanol) is dissolved in only one solvent, where this one solvent is water. In another embodiment, a solvent (such as ethanol) is dissolved in a mixture of only two other solvents. In yet another embodiment, a solvent (such as ethanol) is dissolved in a mixture of only three solvents. In still another embodiment, a solvent (such as ethanol) is dissolved in a mixture of one or more additional solvents, or dissolved in mixture of two or more additional solvents, or dissolved in a mixture of three or more additional solvents. Also, in another embodiment, the solvent (such as ethanol) can be dissolved in a mixture of a plurality of solvents, where one of these is water. Also, the solvent (such as ethanol) can be dissolved in a mixture of a plurality of solvents, where none of these is water. The term "about" preferably means plus or minus 5%. In other embodiments, the term "about" can mean plus or minus 1%, plus or minus 2%, plus or minus 6%, or plus or minus 8%. The term "percent" means by volume. Regarding the above-disclosed solvents, unless specified otherwise, the list does not impose any limitation on which solvent is to be dissolved in which other solvent (or in which plurality of other solvents). In exclusionary embodiments, the compositions, reagents, devices, systems, and methods of the present disclosure can exclude any one or more of the above solvents, and can exclude any one or more of the above solvents at the indicated percentage values, and at the indicated "about" values.

Defining a Solvent by its Dielectric Constant.

The present disclosure provides compositions, reagents, devices, systems, and methods, that comprise one or more polar solvents, one or more non-polar solvents, or that comprise one or more of each of polar and non-polar solvents. Polar solvents have large dipole moments, also known as, "partial charges." They contain bonds between atoms with very different electronegativities, such as oxygen and hydrogen. Non-polar solvents contain bonds between atoms with similar electronegativities, such as carbon and hydrogen, such as octane. Bonds between atoms with similar electronegativities will lack partial charges. This absence of charge which makes these molecules "non-polar." Polarity can be measured by two direct ways. One is through measuring a constant called "dielectric constant." The greater the dielectric constant, the greater the polarity (value for water is high, value for gasoline is low). A second way comes from directly measuring the dipole moment. Polarity is a continuum. While pentane is "non-polar" and water is "polar", there are borderline cases such as diethyl ether, dichloromethane, and tetrahydrofuran (THF) which have both polar and non-polar characteristics. A dividing line between "polar" and "non-polar" is miscibility with water. Diethyl ether and dichloromethane do not mix with water. On the other hand, THF, DMSO, acetonitrile, DMF, acetone and short-chain alcohols do (see, Ashenhurst, James. Substitution Reactions. Masterorganicchemistry dot com). For several nonpolar solvents, the dielectric constants are as follows: pentane (1.8), hexane (1.9), cyclohexane (2.0), benzene (2.4), toluene (2.3), chloroform (4.8), diethylether (4.3). For several polar solvents, the dielectric constants are as follows: acetone (21), demethylformamide (38), acetonitrile (37), ammonia (25), t-butanol (12), ethanol (25) methanol (33), acetic acid (6.2), water (80). The dielectric constants of glycerol (45), ethanol (25), and water (80), and dependence on temperature, are disclosed in, Ponomarenko, Yang, Katsnelson (2009) Effect of high-kappa environment on charge carrier mobility in graphene. Physical Review Letters. 102:206603. The dielectric constant of acetone (20.7) is disclosed by Goto, Kawata, Nakamura, Aoyama (1986) J. Microencapsulation. Vol. 3, Issue 4. In embodiments, the present disclosure provides compositions, reagents, devices, systems, and methods, can include one or more of the above solvents, such as about 20% acetone, about 30% acetone, about 40% acetone, about 50% acetone, about 60% acetone, about 70% acetone, about 80% acetone, about 90% acetone, or about 95% acetone dissolved in a solvent that is water, or 100% acetone. The term "about" can mean plus or minus 5%. The term "percent" means by volume. Regarding the above-disclosed solvents, unless specified otherwise, the list does not impose any limitation on which solvent is to be dissolved in which other solvent (or in which other solvents). In exclusionary embodiments, the compositions, reagents, devices, systems, and methods of the present disclosure can exclude any one or more of the above solvents, and can exclude any one or more of the above solvents at the indicated percentage values, and at the indicated "about" values.

Temperature.

In temperature embodiments, the present disclosure provides compositions, reagents, devices, systems, and methods, that include one or more solvents, such as any of the solvents that are disclosed in the above paragraphs, or in any of the following paragraphs, where the temperature (Centigrade) is 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. What is also provided is a solvent with a temperature that is in a range defined by any of the above two temperatures, such as the range of minus 30 degrees to minus 50 degrees. In exclusionary embodiments, the present disclosure can exclude any solvent that has one of the above temperatures, or it can exclude any composition, reagent, device, system, or method that comprises a solvent having one of the above temperatures.

Also, what is provided is a solvent that has a temperature (Centigrade) of about 20 degrees, about 15 degrees, about 10 degrees, about 5 degrees, about 0 degrees, about minus 5 degrees, about minus 10 degrees, about minus 15 degrees, about minus 20 degrees, about minus 25 degrees, about minus 30 degrees, about minus 35 degrees, about minus 40 degrees, about minus 45 degrees, about minus 50 degrees, about minus 55 degrees, about minus 60 degrees, about minus 65 degrees, about minus 70 degrees, about minus 75 degrees, or about minus 80 degrees. What is also provided is a solvent that has a temperature that is in a range defined by any of the above two temperatures, such as the range of about minus 30 degrees to about minus 50 degrees. The term "about" can mean plus or minus 5 degrees. In exclusionary embodiments, the present disclosure can exclude any solvent that has one of the above temperatures, or it can exclude any composition, reagent, device, system, or method that comprises a solvent that has one of the above temperatures.

In "greater than" embodiments, the present disclosure provides compositions, reagents, devices, systems, and methods, that include one or more solvents, such as any of the above-disclosed solvents has a temperature that is "greater than" 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. "About" embodiments of these "greater than" ranges are also provided by the present disclosure, where "about" means plus or minus five degrees.

In "lesser than" embodiments, the present disclosure provides compositions, reagents, devices, systems, and methods, that include one or more solvents, such as any of the above-disclosed solvents has a temperature that is "lesser than" 20 degrees, 15 degrees, 10 degrees, 5 degrees, 0 degrees, minus 5 degrees, minus 10 degrees, minus 15 degrees, minus 20 degrees, minus 25 degrees, minus 30 degrees, minus 35 degrees, minus 40 degrees, minus 45 degrees, minus 50 degrees, minus 55 degrees, minus 60 degrees, minus 65 degrees, minus 70 degrees, minus 75 degrees, or minus 80 degrees. "About" embodiments of these "lesser than" ranges are also provided by the present disclosure, where "about" means plus or minus five degrees.

Without implying any limitation, in embodiments the present disclosure also encompasses "about" embodiments. Where the word "about" occurs in a claim as originally filed, or where the word "about" is added to a claim by way of amendment, the meaning of the word "about" can be caused to be more precisely defined by way of an amendment that adds one or more of the following limitation to the claim. The word "about" can mean, plus or minus 5%, plus or minus 10%, plus or minus 15%, plus or minus 20%, plus or minus 25%, plus or minus 30%, and so on. Also, the word "about" can mean that a given number that exists in a series of numbers (where the claim includes the word, about) encompasses all values that are between the previous number in the series and the subsequent number in the series. Similarly, the word "about" can mean that a given number in a series of numbers (where the claim includes the word, about) encompasses all values that are half-way and less than half-way in between that number and the immediately previous number in that series, and also encompasses all values that are half-way and less than half-way in between that number and the immediately subsequent number in that series.

In range embodiments, the system, device, compositions, solutions, and methods of the present disclosure encompass a solvent or a solution or a mixture of solvents, that is in one of the following temperature ranges (minus degrees C.): 10-15; 10-20; 10-25; 10-30; 10-35; 10-40; 10-45; 10-50; 10-55; 10-60; 10-65; 10-70: 10-75; 10-80; or 10 to lesser than 80 degrees C. Other temperature ranges (minus degrees C.): 20-25; 20-30; 20-35; 20-40; 20-45; 20-50; 20-55; 20-60; 20-65; 20-70; 20-75; 20-80; or 20 to lesser than 80 degrees C. Even more temperature ranges (minus degrees C.): 25-30; 25-35; 25-40; 25-45; 25-50; 25-55; 25-60; 25-65; 25-70; 25-75; 25-80; or 25 to lesser than 80 degrees C. Still further temperature ranges (minus degrees C.): 30-35; 30-40; 30-45; 30-50; 30-55; 30-60; 30-65; 30-70; 30-75; 30-80; or 30 to lesser than 80 degrees C. And more temperature ranges (minus degrees C.): 35-40; 35-45; 35-50; 35-55; 35-60; 35-65; 35-70; 35-75; 35-80; or 35 to lesser than 80 degrees C. Yet more temperature ranges (minus degrees C.): 40-45; 40-50; 40-55; 40-60; 40-65; 40-70; 40-75; 40-80; or 40 to lesser than 80 degrees C.

In exclusionary embodiment, the present disclosure can exclude any system, device, solution, solvent, mixture of solvents, and method, that is at a temperature within any of the above temperature ranges.

In substance impurity embodiments, the present disclosure can result in a solution, emulsion, composition, slurry, extract, extraction, oil, aqueous solution, where the percentage of a "substance impurity" (percentage by weight within the solution, or emulsion, or extract, etc.) is less than 10% of the total weight, less than 8%, less than 6%, less than 5%, less than 4%, less than 3%, less than 2%, less than 1%, less than 0.8%, less than 0.6%, less than 0.4%, less than 0.2%, less than 0.1%, less than 0.08%, less than 0.06%, less than 0.04%, less than 0.02%, less than 0.01%, less than 0.008%, less than 0.006%, less than 0.004%, less than 0.002%, less than 0.001% of the total weight, and the like. The "substance impurity" can be a substance that is "total pigments," or it can be "chlorophyll," or it can be "total lipids," or it can be the sum of chlorophyll plus waxes, or it can be "waxes," or it can be synthetic pesticides, or the "substance impurity" can refer to the sum of all pigments, lipids, waxes, and synthetic pesticides, and degradants of synthetic pesticides. The skilled artisan understands that the word "pigment" usually means a substance that, to the human eye, has a color such as red, orange, yellow, green, blue, and so on, when present for example at a concentration of about 0.05% in a solution, or at a concentration of about 1.0% in a solution or at a concentration of about 5.0% in a solution.

Duration.

In duration embodiments, the present disclosure encompasses various durations for agitating a mixture of plant matter with a solvent, various durations for soaking plant matter without agitating with a solvent, and various durations for exposing plant matter (exposure time) to solvent without regard to whether or not that is any agitation and without regard to agitation time. Duration can be the time between initial exposure of plant matter to solvent and to the time of substantial removal of solvent from the plant matter. Substantial removal can be, for example, removal of at least 90% of the solvent, or at least 95% of the solvent, for example, by draining through a micromesh filter, or by draining through a plastic polymer filter such as a Millipore® filter, or by removing with centrifugation where the plant matter is collected in a pellet.

Duration can be at least 1 minute, at least 2 min., at least 3 min., at least 4 min., at least 5 min., at least 6 min., at least 8 min., at least 10 min., at least 12 min., at least 14 min., at least 16 min., at least 18 min., at least 20 minutes, and the like.

Also, duration can be about 1 minute, about 2 min., about 3 min., about 4 min., about 5 min., about 6 min., about 8 min., about 10 min., about 12 min., about 14 min., about 16 min., about 18 min., about 20 minutes, and so on.

Duration can be limited to under 1 minute, under 2 min., under 3 min., under 4 min., under 5 min., under 6 min., under 8 min., under 10 min., under 12 min., under 14 min., under 16 min., under 18 min., under 20 min., under 22 min., under 24 min., under 26 min., under 28 min., under 30 minutes, and so on.

The terms "a," "an," "the" and similar referents used in describing the invention are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

Embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A safer and more reliable extraction process for extracting cannabinoids and to reduce chlorophyll and wax co-extraction from a cannabis, or hemp plant substrate comprising, wherein the process excludes use of liquid carbon dioxide, in combination,
    (i) pre-processing comprising lowering the temperature of a solvent to a range of −30 degrees C. to −50 degrees C.,
    (ii) contacting at −30 degrees C. to −50 degrees C., wherein there is a contacting time between the cannabis plant substrate and the solvent to create an emulsion,
    (ill) evaporating for reduction of the emulsion by means of atmospheric evaporation of the solvent,
    (iv) recovering for recovery of the solvent from the emulsion,
    (v) purging under vacuum to remove remaining solvent from the extract whereby a resu tory extract is substantially free of any lipids and chlorophyll,
    wherein optionally,
        (a) the solvent is 95% ethanol and 5% of a solvent that is another solvent that does not comprise ethanol, or
        (b) the solvent is at least one solvent-like material selected from the group consisting essentially of heptane, hexane, isopropyl alcohol, and menthanol.

2. The extraction process of claim 1, wherein the solvent is 95% ethanol and 5% of a solvent that is another solvent that does not comprise ethanol.

3. The extraction process of claim 1, wherein the solvent is at least one solvent-like material selected from the group consisting essentially of heptane, hexane, isopropyl alcohol, and methanol.

4. The process of claim 1,
    wherein there is a pre-processing comprising lowering the temperature of a solvent to a range of −30 degrees C. to −50 degrees C., and wherein there is a contacting at −30 degrees C. to −50 degrees C., that has a contacting time between the plant substrate and the solvent to create an emulsion,
    wherein the contacting at −30 degrees C. to −50 degrees C., is at/east 5 minutes in the range of:
    (i) −30 degrees C. td −35 degrees C.,
    (ii) −35 degrees C. to −40 degrees C.,
    (iii) −40 degrees C. to −45 degrees C., or
    (iv) −45 degrees C. to −50 degrees C.

5. The process of claim 4, wherein the contacting time that is at least 5 minutes in the indicated temperature range is for a period of time in the indicated temperature range that has a continuous and uninterrupted contacting time of:
    (i) 5 minutes to 10 minutes, or
    (ii) 10 minutes to 15 minutes, or
    (iii) 15 minutes to 20 minutes, or
    (iv) 20 minutes to 25 minutes, or
    (v) 5 minutes to 15 minutes, or
    (vi) 5 minutes to 20 minutes.

6. The process of claim 1, wherein the solvent consists of a mixture of ethanol and a non-ethanol solvent, and wherein this mixture is at one of the following ratios, wherein the percentage value is by volume of the ethanol and of the non-ethanol solvent, wherein the volume of the ethanol and the volume of the non-ethanol solvent are each measured prior to mixing the ethanol with the non-ethanol solvent, wherein the ratio is one of;
    (i) 95% ethanol plus 5% non-ethanol solvent,
    (ii) 90% ethanol plus 10% non-ethanol solvent,
    (iii) 85% ethanol plus 15% non-ethanol solvent,
    (iv) 80% ethanol plus 20% non-ethanol solvent, (v) 75% ethanol plus 25% non-ethanol solvent,
(vi) 70% ethanol plus 30% non-ethanol solvent,
(vii) 65% ethanol plus 35% non-ethanol solvent,
(viii) 60% ethanol plus 40% non-ethanol solvent,
(ix) 55% ethanol plus 45% non-ethanol solvent,
(x) 50% ethanol plus 50% non-ethanol, solvent.

7. The process of claim 6, wherein the non-ethanol solvent is water, methanol, isopropyl alcohol, or acetonitrile.

\* \* \* \* \*